United States Patent
DesRosiers

(10) Patent No.: US 6,989,373 B2
(45) Date of Patent: Jan. 24, 2006

(54) METHOD FOR RESTORING A FAT-PAD

(75) Inventor: Eric André DesRosiers, Outremont (CA)

(73) Assignee: Bio Syntech Canada Inc., Laval (CA)

( * ) Notice: Subject to any disclaimer, the term of this patent is extended or adjusted under 35 U.S.C. 154(b) by 315 days.

(21) Appl. No.: 10/055,493

(22) Filed: Oct. 29, 2001

(65) Prior Publication Data

US 2002/0094959 A1 Jul. 18, 2002

Related U.S. Application Data

(60) Provisional application No. 60/248,228, filed on Nov. 15, 2000, and provisional application No. 60/248,570, filed on Nov. 16, 2000.

(51) Int. Cl.
A61K 38/00 (2006.01)
A01N 43/04 (2006.01)
C07K 14/00 (2006.01)

(52) U.S. Cl. .............. 514/21; 514/54; 514/55; 514/560; 530/350; 530/356; 530/421; 530/424

(58) Field of Classification Search .......... 514/21, 514/54, 55, 560; 530/350, 356, 421, 424
See application file for complete search history.

(56) References Cited

PUBLICATIONS

Buschmann et al., Foot & Ankle, vol. 14, pp. 389–394, 1993.*
D'Ambrosia, R.D., Orthopedics, vol. 10, pp. 137–142, 1987.*
Van Schie et al., Diabetes Care, vol. 23, pp. 634–638, 2000.*
Aerts, P., et al., Journal of Biomechnics, 28: 1299–1308, 1995.
Alexander, R. McN., et al., Journal of Zoology –London A:209: 405–419, 1986.
Balkin, S.W., Fluid silicone implantation of the foot. In Neale's common foot disorders: diagnosis and management. 5th ed. Lorimier, D., Churchill Livingstone, U.K., 387–400, 1997.
Bennett, M.B. and Ker, R.F., Journal of Anatomy, 171: 131–138, 1990.
Blechschmidt, E., Die Architektur des Fersenpolsters. Gegenbaurs Morphologisches Jurhbuch, 73: 20–68, 1934 (translated and re–edited as: Blechschmidt, E., The Structure of the Calcaneal Padding. Foot & Ankle, 2: 260–283, 1982).
Buschmann, W.R., et al., Foot & Ankle, 14: 389–394, 1993.
Buschmann, W.R., et al., Foot & Ankle, 16: 254–258, 1995.
D'Ambrosia, R.D., Orthopedics, 10:137–142, 1987.
Jahss, M.H., et al., Foot & Ankle, 13: 227–232, 1992.
Ker, R.F., Journal of Experimental Biology, 199 (Pt 7): 1501–1508, 1996.
Narvaez, J.A., et al., Radiographics, 20: 333–352, 2000.
Van Schie, C.H.M., et al., Diabetes Care, 23: 634–638, 2000.

* cited by examiner

*Primary Examiner*—Jon Weber
*Assistant Examiner*—Abdel A. Mohamed
(74) *Attorney, Agent, or Firm*—Nixon Peabody LLP

(57) ABSTRACT

The present invention relates to a method for treating damaged or degenerated fat pads in a foot of a host in need thereof. The method comprises the step of injecting into the fat pad of the host a biocompatible solution having physico-chemical and mechanical properties substantially similar to a fatty acid mixture normally present in a healthy fat pad.

29 Claims, 3 Drawing Sheets

FIG_1

METHOD FOR RESTORING A FAT-PAD

This application claims the benefit under 35 U.S.C. § 119(e) of U.S. Ser. No. 60/248,228, filed Nov. 15, 2000, and U.S. Ser. No. 60/248,570, filed Nov. 16, 2000.

BACKGROUND OF THE INVENTION (a) Field of the Invention

The present invention describes a method for restoring the thickness of a damaged or degenerated fat-pad.

(b) Description of Prior Art

Heel pain is a common complaint that leads, every year, about 1% of the North-American population to consult a physician. The pain is most often due to plantar fasciitis or to heel spurs. Those conditions can usually be traced to accidents or specific activities, but are often aggravated by an atrophy of the calcaneal fatty pad. This fat-pad cushion plays a critical biomechanical role in absorbing the impact of walking and running by distributing the load and absorbing energy upon impact.

The fat-pads are cushions made of communicating pockets of fascia filled with fatty acids. Anatomically, three distinct fatty pads can be clearly identified below the plantar surface, at the three contact points with the ground, i.e. under the heel, on the metatarsal head, and on the outer arch contact area.

Blechschmidt (Blechschmidt, E., Die Architektur des Fersenpolsters. Gegenbaurs Morphologisches Jarhbuch, 73: 20–68, 1934 (translated and re-edited as: Blechschmidt, E., The Structure of the Calcaneal Padding. Foot & Ankle, 2: 260–283, 1982) performed a thorough study, using sagittal, frontal as well as horizontal sections to map the anatomical structure of those pads throughout the development of foetus and adults. This work documented well the structure of the pads, and brought the first clues on how this would relate to their physiological role. The pads are composed of septa forming a trabecular network of intercommunicating chambers. Those chambers are disposed in whorls, which follow the curvature and torsion of the calcaneus itself. This arrangement suggested some form of biomechanical optimisation.

Most attempts to study the biomechanics of the heel pad were based on the load-deformation curves obtained from in vivo impact experiments, through pendulum and drop tests, or by using force platform. Others performed in vitro experiments (Bennett, M. B. and Ker, R. F., Journal of Anatomy, 171: 131–138, 1990; and Aerts, P., et al., Journal of Biomechanics, 28: 1299–1308, 1995; and Ker, R. F., Journal of Experimental Biology, 199(Pt 7):1501–1508, 1996). All results highlighted the efficiency of the pads to cushion the musculoskeletal system from ground-heel impacts, and brought some insight into the comprehension of the pads' physiological role in the biomechanics of the foot. It then appeared that the heel fat pad has a structure optimised for load bearing (Jahss, M. H., et al., Foot & Ankle, 13: 227–232, 1992).

Further information came from studying the fatty acid composition of the heel fat pad (Buschmann, W. R., et al., Foot & Ankle, 14: 389–394, 1993). Using capillary gas-liquid chromatography, this group determined that the fat pads of normal individuals is mainly composed of the following mixture of fatty acids:

TABLE 1

Fatty acid composition of the heel fat pad

| Fatty acid | fraction | S.D. |
| --- | --- | --- |
| Myristate | 1.6% | 0.5% |
| Palmitate | 13.6% | 2.2% |
| Stearate | 1.5% | 0.8% |
| Palmitoleate | 10.6% | 1.9% |
| Vaccenate | 4.1% | 1.1% |
| Oleate | 40.6% | 2.4% |
| Linoleate | 14.6% | 2.8% |
| Sum: | 86.6% | |

The physiological mechanics of the pads relies on the motion of fatty acids constrained within a complex septal system. This system is analogous to a mechanical dashpot. Its characteristics depend on the porosity of the trabecular network, studied by Blechschmidt (Blechschmidt, E., Die Architektur des Fersenpolsters. Gegenbaurs Morphologisches Jarhbuch, 73: 20–68, 1934 (translated and re-edited as: Blechschmidt,E., The Structure of the Calcaneal Padding. Foot & Ankle, 2: 260–283, 1982)), and on the properties of the fatty acids (Buschmann, W. R., et al., Foot & Ankle, 14: 389–394, 1993). The ratio of unsaturated fatty acids to saturated fatty acids indeed affects the properties of the fat, and modifies the biomechanical properties of the pads (Jahss, M. H., et al., Foot & Ankle, 13: 227–232, 1992).

The fat pads normally become atrophic with age (D'Ambrosia, R. D., Orthopedics, 10:137–142, 1987; and Jahss, M. H., et al., Foot & Ankle, 13: 227–232, 1992), but the risk of premature atrophy increases if the individual is overweight, has diabetes (Alexander, R. McN., et al., Journal of Zoology—London, A209: 405–419, 1986), has often worn thin-sole or high-heel shoes. Also, the treatment of plantar fasciitis with cortisone injections leads to further atrophy of the pads (D'Ambrosia, R. D., Orthopedics, 10:137–142, 1987). Atrophic cushions usually have reduced height due to a loss of fatty acid substance, or from herniation of the fascia (Buschmann, W. R., et al., Foot & Ankle, 16: 254–258, 1995). Thin fat pads can be very uncomfortable, and can lead to painful pathologies (Narváez, J. A., et al., Radiographics, 20: 333–352, 2000). A comparative experiment on 200 heel pads demonstrated that the feet with thinnest fat pads also had the lowest shock absorbency.

Plantar injections of silicone fluid have been used to relief localised pressure-related foot disorders, such as corns and calluses (Balkin, S. W., Fluid silicone implantation of the foot. In Neale's common foot disorders: diagnosis and management. 5th ed. Lorimier, D., Churchill Livingstone, U.K., 387–400, 1997) and to reduce risk factors for ulceration in diabetic foot (Van Schie, C. H. M., et al., Diabetes Care, 23: 634–638, 2000). Silicone is engulfed and retained within histocyte cell body as microscopic droplets, and stimulates the local deposition of collagen fibres. It thickens the skin at the site of injection, by inducing the local formation of scar-like fibrous tissue. It is not compatible with the normal fatty acid composition, and does not participate in restoring the normal physiological function of the fat pad.

The ageing and active segments of the population are especially affected by fat pad atrophy. With the normal loss of fat pads, pressure area starts developing over the metatarsal and the heel area as early as age 30 (D'Ambrosia, R. D., Orthopedics, 10:137–142, 1987). The individuals suffering from this condition currently rely only on orthoses and in-sole cushioning. It would thus be highly desirable to develop a method for restoring the thickness of the pads, and consequently their cushioning function.

SUMMARY OF THE INVENTION

One object of the present invention is to provide a new method for restoring the thickness of the pads, and consequently their cushioning function.

In accordance with the present invention, it was thus found that the thickness of fat pads can be restored by the injection of an appropriate solution. Such a solution needs to be physico-chemically and mechanically similar to the fatty acid mixture normally present in the fat pads in order to participate in its biomechanical function. Fat-pads are not only present in the foot but also in other part of the human body. The present invention thus encompasses not only fat-pads of the foot but also from other parts of the human body.

The solution also needs to be injectable, non-toxic, biocompatible, and to have a sufficiently long residence time in the pad to provide a safe and long lasting effect.

In accordance with the present invention, there is therefore provided a method for treating damaged or degenerated fat pads of a host in need thereof, said method comprising injecting into the fat pad of said host a biocompatiable solution substantially similar to a fatty acid mixture normally present in a healthy fat pad, said solution having an intrinsic viscosity above 5 mPa.s when measured at physiological temperature.

DETAILED DESCRIPTION OF THE INVENTION

The present invention aims at restoring fat pads of the foot by injecting an appropriate solution into such fat pads.

The term "fat pads" refers herein to any cushions made of communicating pockets of fascia and filled with fatty acids that are present in humans and mammalians. "Atrophic fat pad" describes a normal mature fat pad that underwent a reduction of volume, weight, thickness or size (Ex: loss of fatty acids).

The term "restoring" refers herein to the action of bringing back, totally or partly, specific normal physiological properties such as the physico-chemical, the physical (thickness), the mechanical or the physiological functions (cushioning).

The term "cushioning" refers herein to the capacity of the pad to dissipate impact energy.

The term "biocompatible" refers herein to the quality of a solution that can be compatible with biological tissues, that is not toxic to biological tissues, and that is tolerated by the biological tissues.

The term "solution" refers herein to any liquid, organic or aqueous, low to high viscosity systems, to any dispersions of solids into liquid, organic or aqueous, low to high viscosity systems, and to any gelled, organic or aqueous, extrudable or injectable, systems. Such solutions may comprise soluble small-size molecules, soluble monomers, soluble oligomers, soluble polymers and copolymers as well as nonsoluble solid organic or mineral entities such as microparticles or nanoparticles.

The term "autologous solution" refers herein to any liquid that is autologous to a patient to be treated, or that origin from the patient to be treated.

The term "vehicle" refers herein to any liquid chemicals, either organic or aqueous. "Metabolically absorbable vehicle" refers to any vehicles, as described above, that are readily and completely eliminated or consumed in vivo through normal metabolic pathways: for example, water, isopropyl alcohol, etc.

"Polymer" generally covers all molecules relative to macromolecular or polymer chemistry: polymers, copolymers, macromolecular chains, synthetic, biopolymers, artificial polymers, etc.

"Self-gelling" refers to the ability of turning into gels under specific conditions such as the internal composition or/and the action of external stimuli. It comprises pH-triggered or pH-controlled gelling, thermo-gelling, ionic gelling, and the like.

In the present invention, a solution for restoring the fat pads of the foot is made of a mixture of fatty acids normally present in human fat pads. The relative proportion of each fatty acid is determined to:
1) match the natural fatty acid composition of the fat pad, such as measured by Buschmann et al. (supra), or
2) to achieve mechanical properties similar to those of the natural fatty acid composition of the fat pad.

Figure 1:
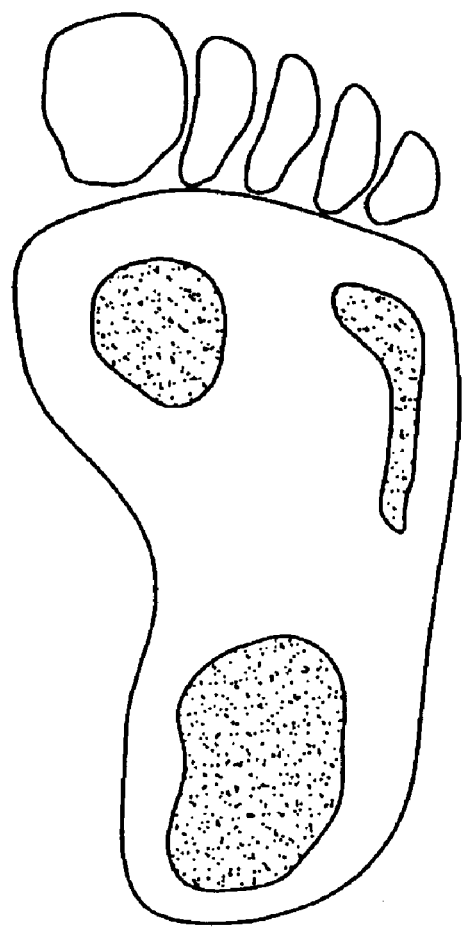
FIG. 1 illustrates fat-pads found in a foot of a Human.
Figure 2:
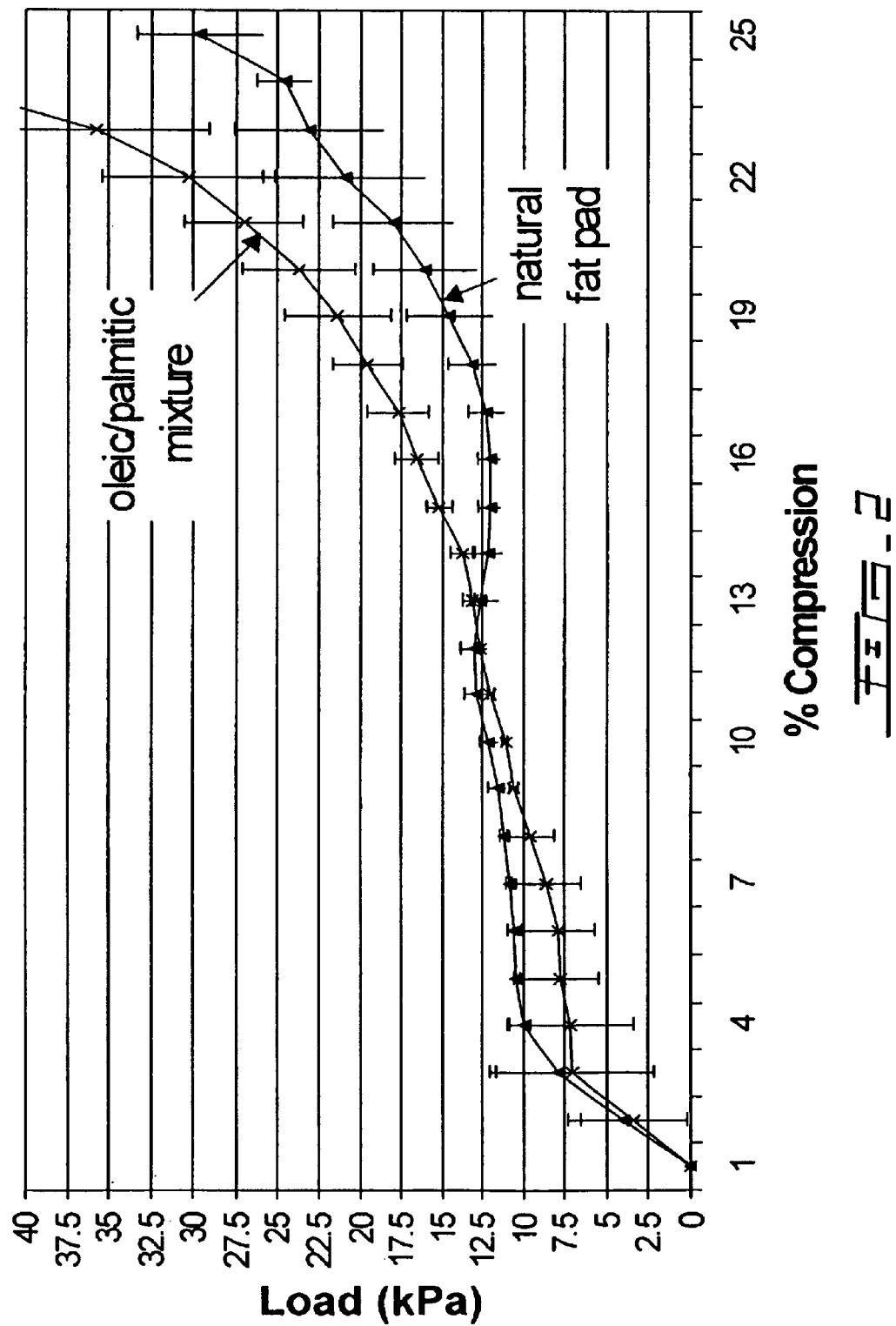
FIG. 2 illustrates a graph showing a comparison of the mechanical properties of the natural fat pad fatty acid mixture, and of a simplified 2 fatty acids formulation, at room temperature (22.0±0.5° C.)

In that last case, a simplified mixture can be used. In accordance with the present invention, it was found that an appropriate mix of one saturated and one unsaturated fatty acids, such as 17% palmitic acid and 83% oleic acid (w/w), yields a similar stress-strain curve (FIG. 2).

The fatty acids are weighed, combined in a container, warmed to melt the components, and mixed. The solution can be sterilised by an appropriate method, preferably by filtering the warm solution through 0.2 μm filter.

Figure 3:
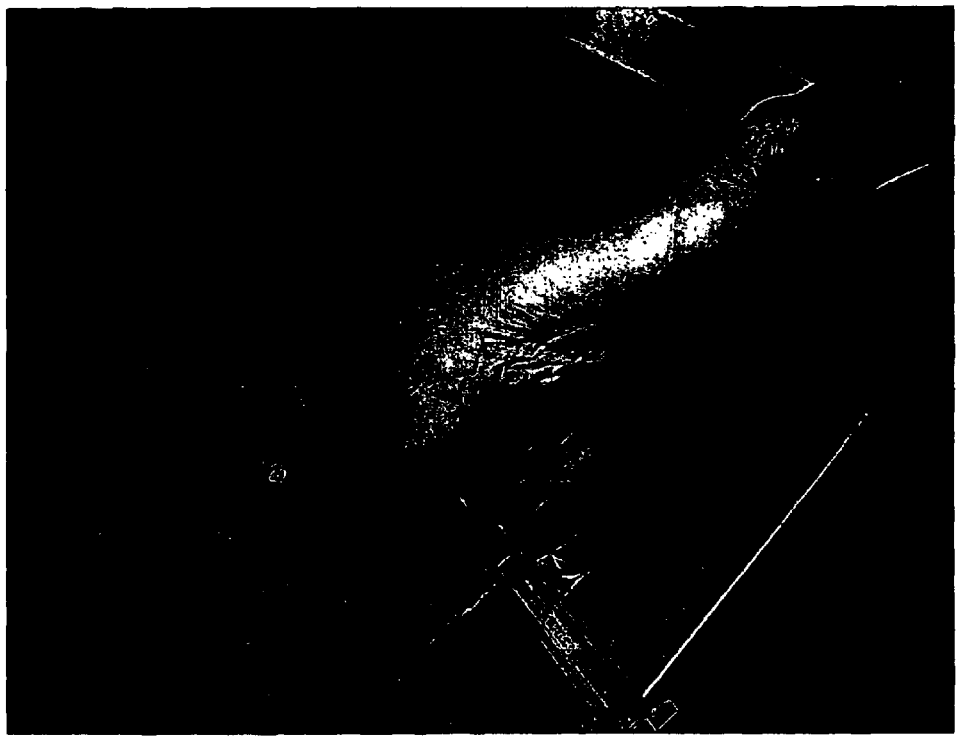
FIG. 3 illustrates a preferred mode of administration in a heel of a patient, of a composition in accordance with the present invention.

In order to prove the feasibility of the approach of fat pad restoration by injecting fatty acid mixture, a syringe containing a coloured (Oil red) mixture of fatty acids, mimicking the normal composition of the pad was used for injection in cadavers: myristate 1.9%, palmitate 15.9%, stearate 1.7%, palmitoleate 12.3%, vaccenate 4.8%, oleate 46.4% and linoleate 17.0% (w/w). The content of the syringe was melted under tap water and injected in the three fat pads of each foot with a standard length needle (2–3 cm). As a general rule, the pads can be reached by inserting a needle about 1 cm below the skin surface at the three main pressure points of the foot (FIG. 3). The needle first goes through the thick plantar dermis before reaching the softer underlying fat pads. It is therefore simple to feel when the needle goes through the dermis and reaches the fat pad. The fat pad under the heel is 1.6–2.0 cm thick. There is a small (about 0.5 mm thick) synovial burse between the pad and the calcaneum—which should be avoided. It is easy to evaluate clinically if this compartment has been inadvertently punctured. There is no burse at the two other pad sites.

Figure 4:
FIG. 4 illustrates an injected coloured fatty acid composition in the pad in accordance with one embodiment of the present invention.

Following massaging, this injection procedure consistently resulted in having the dye spreading in the entire pads (FIG. 4), without dispersing into the other tissues. This confirms the interconnectivity of the pads' trabaecular structure, and demonstrates their confinement by an external capsule.

The clinician can feel the increased resistance in the syringe as the fat pad becomes refilled. The volumes of solution that could be injected in this cadaver study are reported in Table 2. The reported volume denotes the approximate volume injected until the piston of the syringe could no longer be pushed, making the pad starting to feel rigid.

TABLE 2

Injectable volumes of solution

| Vol. Injected/site (ml, Left/Right) | Young (~20 y) | Middle-age (~50 y) | Old (~70 y) |
|---|---|---|---|
| Heel | 1/1.5 | 2/3 | 5/nd |
| Ball | 1/1 | 1/1 | 2/nd |
| Arch | 0.5/1 | 1/1 | 2/nd |

In a preferred embodiment of the present invention, the method of restoring the functionality of the fat pads of the foot comprises the step of injecting a solution into the sub-calcaneal fat pad, also called heel fat pad, and/or the outside arch fat pad, and/or the metatarsal fat pads, also called ball fat pad, or any necessary combined injections in such fat pads. The method also supports any further possible periodical injections of said solution into such fat pads that may be necessary to long-term therapeutic treatments.

In accordance with the present invention, there is provided a method for restoring the thickness of atrophic damaged or degenerated fat-pads of the foot with an injectable solution. The method comprises the steps of a) injecting a solution in the sub-calcaneal (heel), outside arch, or metatarsal (ball) fat pads of the foot; b) restoring first the thickness of the natural pad; and c) providing a durable thickness increase of the pad for a long enough time, from a few weeks to permanence.

In one preferred embodiment, the solution comprises one or more natural or unnatural saturated and mono- or poly-unsaturated fatty acids, that are selected preferably in a group consisting of palmitate, stearate, myristate, palmitoleate, oleate, vaccenate, linoleate, and the like, and their acyclic, cyclic, heterocyclic, aromatic ester derivatives containing one or more groups such as hydroxy, acyloxy, aryloxy, amino, sulfhydryl, sulfonate, sulfate, phosphonate, phosphate, bis-, tris- and poly-phosphonates and phosphates, phosphatidyl, nucleosides, oligosaccharides, polysaccharides, polyols, and the like, and a mixture thereof. The solution may additionally contain a pharmaceutical agent.

In one preferred embodiment, the fatty acid component is mixed with an appropriate metabolically absorbable liquid vehicle to reduce viscosity and allow injectability at room temperature.

The fatty acid solution may comprise a metabolically absorbable liquid vehicle selected in a group consisting of water, alcoholic solvents, alkylene glycols, poly-alcohols, and the like. The metabolically absorbable liquid vehicle is more preferably selected in a group consisting of ethanol, isopropyl alcohol, ethylene glycol, glycerol, and the like, and any mixture thereof.

In one preferred embodiment, the solution comprises oleoate and palmitate. The solution may be under gel or solid form at low to room temperature, e.g. 20 degrees Celsius and below, but may become more or less a viscous liquid at higher temperatures, e.g. above 35–40 degrees Celsius. For example, the solution may be stored as a gel at a temperature below the physiological temperature and heated above the physiological temperature prior to use in order for the solution to be injectable.

In another preferred embodiment, the solution becomes highly viscous or turns into a gel after being injected into the pad by one of the following processes: a) Gelling: the solution is injected as a liquid, and later turns in situ into a gel, within the pad; b) Polymerisation in situ: the solution containing monomers and/or oligomers, or a mixture of two or more different monomers, is injected as a liquid, and later polymerises or co-polymerises in situ, within the pad; c) Concentration: the solution contains a viscous component mixed with an appropriate metabolically absorbable liquid vehicle, to reduce viscosity and to allow injectability, the solvent or vehicle, after injection in the pad, being absorbed in the organism, thus increasing the concentration and hence the viscosity of the viscous component.

In another embodiment, the solution is a self-gelling solution such as a stimuli-triggered self-gelling polymeric solution, and preferably a thermo-gelling solution. This thermo-gelling solution may be a thermo-gelling chitosan-based aqueous system as described in International Application published as WO99/07416. Such self-gelling solutions may be liquid at low to room temperature, e.g. 20 degrees Celsius or below, and may form a solid gel at a higher temperature, e.g. above 30 degrees Celsius. Inversely, such self-gelling solutions may be liquid at high temperatures, e.g. above 40 degrees Celsius, but may form a gel at a lower temperature, e.g. below 40 degrees Celsius. Typical thermo-gelling polymeric solutions may be designed with polymers selected among poly(acrylic acid), methyl cellulose, hydroxyethyl cellulose, hydroxypropyl methyl cellulose, poly(ethylene oxide)-based triblock copolymers, chitosan, etc. The method does not exclude any other injectable self-forming systems, e.g. Lower critical solution temperature (LCST), liquid crystalline, polymer precipitation (solid), precipitation in situ, coagulation, etc.

In another embodiment, the solution comprises a polymer such as an artificial or synthetic polymer, or one of its derivatives, with an appropriate metabolically absorbable liquid vehicle, such as water. The polymer may be selected in a group consisting of cellulose and its substituted derivatives, poly(ethylene glycol) and poly(propylene glycol) and its copolymers, poly(ethylene glycol) copolymers with other synthetics such as poly(hydroxy acids), poly(vinyl alcohol), poly(vinyl pyrrolidone), and the like, and the mixture thereof.

In a same way, the solution may comprise a biopolymer such as a polysaccharide or a polypeptide, or one of its derivatives, with an appropriate metabolically absorbable liquid vehicle, such as water. The solution may comprise hyaluronic acid or collagen, or one of their derivatives, or a mixture thereof, with an appropriate metabolically absorbable liquid vehicle, such as water. The solution may be formulated with elements selected from the group consisting of fatty acids, thermo-gelling chitosan-based solution, collagen or derivative, hyaluronic acid, poly(ethylene glycol), and an appropriate metabolically absorbable liquid vehicle. Other biopolymers may comprise polylysine, gelatin, chitosan, alginate, chondroïtin sulfate, and the like.

The solution may comprise an aqueous liquid or a non-aqueous liquid. Aqueous (water-based) solutions are commonly observed. Biocompatible liquid vehicle may be used such as water-soluble and water-insoluble solvents or liquid chemicals, e.g. ethyl lactate, ethyl acetate, glycerol formal, triacetin, N-methyl-pyrrolidone, propylene carbonate, dimethyl sulfoxide, alkylene glycols (ethylene glycol), glycerol, ethanol, isopropyl alcohol, alcoholic solvents, polyalcohols, and the like.

In the method of the present invention, the solution is generally administered to the fat pads by injecting from a needle/syringe system. Any devices that enable to percutaneously administer the solution to the pads may prove to be appropriate. The solution may be injected using any devices designed for administering injectable fillers.

It is intended that the method described herein can be applied similarly to any other fat pads of human and mammalian bodies, such fat pads being defined as being closed cushions of communicating chambers filled with fatty acids, for restoring totally or partly the physical functions of atrophic, damaged or degenerated pads with an injectable solution, by injecting in the pad and restoring first the thickness of the natural pad for a long enough time, from a few weeks to permanence.

The present invention will be more readily understood by referring to the following examples which are given to illustrate the invention rather than to limit its scope.

EXAMPLE I

A mixture is formulated according to the natural fatty acid composition of the fat pad. Specifically, the fatty acid ratios are determined according to the relative proportions of fatty acids measured by Buschmann et al. (supra), and reported to a total of 100%: myristate 1.9%, palmitate 15.9%, stearate 1.7%, palmitoleate 12.3%, vaccenate 4.8%, oleate 46.4% and linoleate 17.0% (w/w).

The fatty acids are weighed, combined in an amber glass bottle, warmed to 65° C. in a water bath and mixed using a magnetic stir plate. The mixture is sterilised by filtration on a 0.2 $\mu$m filter, and dispensed in aseptic conditions, by 5 ml aliquots, in amber glass vials, to avoid photo-oxidation.

Each vial, stored at or below room temperature, can be used by first warming it up slightly above the melting point of the mixture (37–40° C.), using warm tap water or another moderate source of warmth. The liquified solution is then drawn from the vial with a 5 ml syringe fitted with a fine needle (26G).

The plantar surface of the patient's foot is washed with soap, rinsed with water, dried, and prepared with 70% isopropyl alcohol and a sterile gauze wipe. The site of injection can first be anaesthetised with an appropriate solution, such as Mepivacaine 3%.

The solution is then injected within the atrophic fat pad, at about 1 cm below the surface of the skin. For the heel site, this injection site is directly above the calcaneus, where heel spur normally develops.

The clinician can feel the increased resistance in the syringe as the fat pad becomes refilled.

EXAMPLE II

The mixture is a simple combination of a few fatty acids normally present in human foot fat pads. The mixture is formulated in order to achieve mechanical properties similar to those of the natural fatty acid composition of the fat pad. An appropriate mix of saturated and unsaturated fatty acids, such as 17% palmitic acid and 83% oleic acid (w/w), can achieve this goal.

The fatty acids are weighed, combined in an amber glass bottle, warmed to 65° C. in a water bath and mixed using a magnetic stir plate. The mixture is sterilised by filtration on a 0.2 $\mu$m filter, and dispensed in aseptic conditions, by 5 ml aliquots, in amber glass vials, to avoid photo-oxidation.

Each vial, stored at or below room temperature, can be used by first warming it up slightly above the melting point of the mixture (37–40° C.), using warm tap water or another moderate source of warmth. The liquefied solution is then drawn from the vial with a 5 ml syringe fitted with a fine needle (26G).

The plantar surface of the patient's foot is washed with soap, rinsed with water, dried, and prepared with 70% isopropyl alcohol and a sterile gauze wipe. The site of injection can first be anaesthetised with an appropriate solution, such as Mepivacaine 3%.

The solution is then injected within the atrophic fat pad, at about 1 cm below the surface of the skin. For the heel site, this injection site is directly above the calcaneus, where heel spur normally develops.

The clinician can feel the increased resistance in the syringe as the fat pad becomes refilled.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for treating a damaged or degenerated fat pad of a host in need thereof, said method comprising injecting into the fat pad of said host a biocompatible solution, with an intrinsic viscosity above 5 mPa·s at physiological temperature, wherein said solution is composed of at least one fatty acid selected from the group consisting of a natural or unnatural saturated fatty acid and a mono or poly unsaturated fatty acid.

2. The method of claim 1, wherein the fat pad is located in the sub-calcaneal, outside arch or metatarsal of a foot.

3. The method of claim 1, wherein the saturated fatty acid is selected from the group consisting of palmitate, stearate, and myristate, and acyclic, cyclic, heterocyclic, aromatic ester derivatives thereof, wherein the derivatives are selected from the group consisting of from hydroxy, acyloxy, aryloxy, amino, sulfhydryl, sulfonate, sulfate, phosphonate, phosphate, bis-, tris- and poly-phosphonates and phosphates, phosphatidyl, nucleosides, oligosaccharides, polysaccharides, and polyols.

4. The method of claim 1, wherein the unsaturated fatty acid is selected from the group consisting of palmitoleate, oleate, vaccenate and linoleate, and acyclic, cyclic, heterocyclic, aromatic ester derivatives thereof, wherein the derivatives are selected from the group consisting of hydroxy, acyloxy, aryloxy, amino, sulfhydryl, sulfonate, sulfate, phosphonate, phosphate, bis-, tris- and poly-phosphonates and phosphates, phosphatidyl, nucleosides, oligosaccharides, polysaccharides, and polyols.

5. The method of claim 1, wherein said solution is an autologous solution.

6. The method of claim 1, wherein said solution comprises at least palmitate and oleate.

7. The method of claim 1, wherein said solution comprises a polymer and a metabolically absorbable liquid vehicle.

8. The method of claim 1, wherein said solution comprises an aqueous liquid.

9. The method of claim 1, wherein said solution comprises a non-aqueous liquid.

10. The method of claim 1, wherein said solution forms a gel at a temperature above 30° C.

11. The method of claim 1, wherein said solution is a thermo-gelling chitosan-based solution.

12. The method of claim 1, wherein said solution comprises hyaluronic acid, and a metabolically absorbable liquid vehicle.

13. The method of claim 1, wherein said solution comprises collagen, and a metabolically absorbable liquid vehicle.

14. The method of claim 1, wherein said solution comprises components selected from the group consisting of fatty acids, thermogelling chitosan-based solution, collagen, hyaluronic acid, poly(ethylene glycol), and a metabolically absorbable liquid vehicle.

15. The method of claim 1, wherein said solution is liquid at a temperature of and below 20 degrees Celsius, but forms a gel at temperatures above 30 degrees Celsius.

16. The method of claim 1, wherein said solution is pre-heated at a temperature between 35 and 45 degrees Celsius to be liquid and injectable.

17. The method of claim 1, wherein said solution is a gel at the time of injection.

18. The method of claim 1, wherein said solution is injected into the fat pad by use of a syringe and a hypodermic needle.

19. The method of claim 1, wherein said method is repeated periodically.

20. The method of claim 1, wherein said fatty acids are mixed with a metabolically absorbable liquid vehicle.

21. The method of claim 20, wherein the liquid vehicle is selected from the group consisting of water, alcoholic solvent, alkylene glycol and poly-alcohol.

22. The method of claim 20, wherein the liquid vehicle is at least one member selected from the group consisting of ethanol, isopropyl alcohol, ethylene glycol and glycerol.

23. The method of claim 1, wherein said solution becomes viscous or turns into a gel after injection.

24. The method of claim 23, wherein the solution comprises monomers and/or oligomers, or a mixture of at least two different monomers and polymerises or co-polymerises within the pad after injection.

25. The method of claim 23, wherein the solution comprises a viscous component mixed with a metabolically absorbable liquid vehicle, wherein after injection, the vehicle is absorbed in the host, thus increasing the concentration and hence the viscosity of the solution component.

26. The method of claim 1, wherein the solution comprises a polymer.

27. The method of claim 26, wherein the polymer is selected from the group consisting of cellulose, a substituted cellulose, poly(ethylene glycol) poly(propylene glycol), a copolymer of poly(ethylene glycol), a copolymer of poly(propylene glycol), a poly(ethylene glycol) copolymer with a poly(hydroxy acid), a poly(vinyl alcohol), or a poly(vinyl pyrrolidone), or a mixture thereof.

28. The method of claim 26, wherein the biopolymer is selected from the group consisting of a polysaccharide and a polypeptide.

29. The method of claim 28, wherein the biopolymer is selected from the group consisting of collagen, hyaluronic acid, poly(ethylene glycol), polylysine, gelatin, chitosan, alginate, and chondroitin sulfate.

* * * * *